US009364364B2

(12) United States Patent  (10) Patent No.: US 9,364,364 B2
Williams  (45) Date of Patent: Jun. 14, 2016

(54) SIMPLE PROSTHESIS FOR MANUALLY-CHALLENGED PERSONS

(71) Applicant: Faye Annette Williams, Inglewood, CA (US)

(72) Inventor: Faye Annette Williams, Inglewood, CA (US)

(*) Notice: Subject to any disclaimer, the term of this patent is extended or adjusted under 35 U.S.C. 154(b) by 0 days.

(21) Appl. No.: 13/932,117

(22) Filed: Jul. 1, 2013

(65) Prior Publication Data

US 2015/0005898 A1    Jan. 1, 2015

(51) Int. Cl.
  A61F 13/00    (2006.01)
  A61F 13/06    (2006.01)
  A61F 5/01     (2006.01)

(52) U.S. Cl.
  CPC ................... *A61F 5/0118* (2013.01)

(58) Field of Classification Search
  CPC ................................... A61F 5/0118
  USPC ...................................... 602/60–64
  See application file for complete search history.

(56) References Cited

U.S. PATENT DOCUMENTS

| | | | | |
|---|---|---|---|---|
| 1,547,179 A * | 7/1925 | Martens | ......... | 401/201 |
| 3,942,194 A * | 3/1976 | Winter | ......... | 623/65 |
| 4,154,542 A * | 5/1979 | Rasmason | ......... | 401/7 |
| 4,447,912 A * | 5/1984 | Morrow | ......... | 2/159 |
| 4,494,660 A * | 1/1985 | Hansen | ......... | 211/69.1 |
| 4,523,781 A * | 6/1985 | Brody | ......... | 294/25 |
| 4,602,885 A * | 7/1986 | Bischoff | ......... | B43L 15/00 15/437 |
| 5,050,999 A * | 9/1991 | Van Loon, III | ......... | A45C 3/045 383/117 |
| 5,345,613 A * | 9/1994 | Jones | ......... | A41B 11/00 2/240 |
| 5,845,994 A * | 12/1998 | Rice | ......... | A45C 1/04 224/602 |
| 6,264,391 B1 * | 7/2001 | Kroha | ......... | 401/201 |
| 6,292,949 B1 * | 9/2001 | Chang | ......... | 2/159 |
| 2004/0186402 A1 * | 9/2004 | Bennett | ......... | 602/21 |
| 2008/0034479 A1 * | 2/2008 | Barnett | ......... | A41B 11/02 2/241 |

* cited by examiner

*Primary Examiner* — Kristen Matter

(57) ABSTRACT

A simple and inexpensive prosthetic device for manually challenged patients comprising a tube of moderately elastic material which can be stretched over a portion of the patient's anatomy, such as a hand, forearm stub or the like, and which can receive and firmly hold a variety of tools to enable the patient to perform numerous tasks which normally require the use of fingers.

1 Claim, 7 Drawing Sheets

SIMPLE PROSTHESIS FOR MANUALLY-CHALLENGED PERSONS

FIELD OF INVENTION

This invention relates to prosthetic devices and is particularly directed to simple prosthetic devices for manually challenged persons.

BACKGROUND

Each year many thousands of people become manually challenged due to crippling illnesses, such as arthritis, Parkinson's disease and the like, or by partial or complete amputation of their hands by surgery, fire, explosion, automobile or industrial accidents or other causes. Medical science has developed highly sophisticated prosthetic device which can enable manually challenged patients to perform substantially as well as unchallenged persons. However, these sophisticated prosthetic devices require many months to produce and fit to the patient, followed by many more months of years of training and physical therapy in learning and developing the ability to use these devices. Also, even after the patient is thoroughly familiar with the use of these sophisticated prosthetic devices, considerable time and effort are required to put o or take off these devices. Consequently, manually challenged patients are forced to endure extensive periods of time when they must suffer from their loss. Furthermore, the cost of such sophisticated prosthetic devices is extremely high and is prohibitive for many patients. Thus, none of the prior art prosthetic devices have been entirely satisfactory.

BRIEF SUMMARY AND OBJECTS OF INVENTION

These disadvantages of the prior art are overcome with the present invention and improved prosthetic devices are provided which are inexpensive to produce and purchase and which are quick and simple to install and use requiring little, if any, learning and training.

These advantages of the present invention are preferably attained by providing simple and inexpensive prosthetic devices which can be installed or removed in seconds and which enable the patient to firmly grip and maneuver a variety of tools using primarily shoulder muscles.

In accordance with the present invention, these advantages are preferably attained y providing tubes of moderately elastic material which can be stretched over a portion of the patient's anatomy, such as a hand, forearm stub or the like, and which can receive and firmly hold a variety of tools to enable the patient to perform numerous tasks which normally require the use of fingers.

Accordingly, it is an object of the present invention to provide improved prosthetic devices for manually challenged patients.

Another object of the present invention is to provide simple and inexpensive prosthetic devices for manually challenged patients A further object of the present invention is to provide simple and inexpensive prosthetic devices for manually challenged patients which can be installed or removed in seconds.

An additional object of the present invention is to provide simple and inexpensive prosthetic devices for manually challenged patients which can firmly grip a variety of tools to enable the patients to perform numerous tasks which normally require the use of fingers.

A specific object of the present invention is to provide simple and inexpensive prosthetic devices for manually challenged patients comprising tubes of moderately elastic material which can be stretched over a portion of the patient's anatomy, such as a hand, forearm stub or the like, and which can receive and firmly hold a variety of tools to enable the patient to perform numerous tasks which normally require the use of fingers.

These and other objects and features of the present invention will be apparent from the following detailed description, taken with reference to the figures of the accompanying drawings.

DETAILED DESCRIPTION OF THE INVENTION

Figure 1:
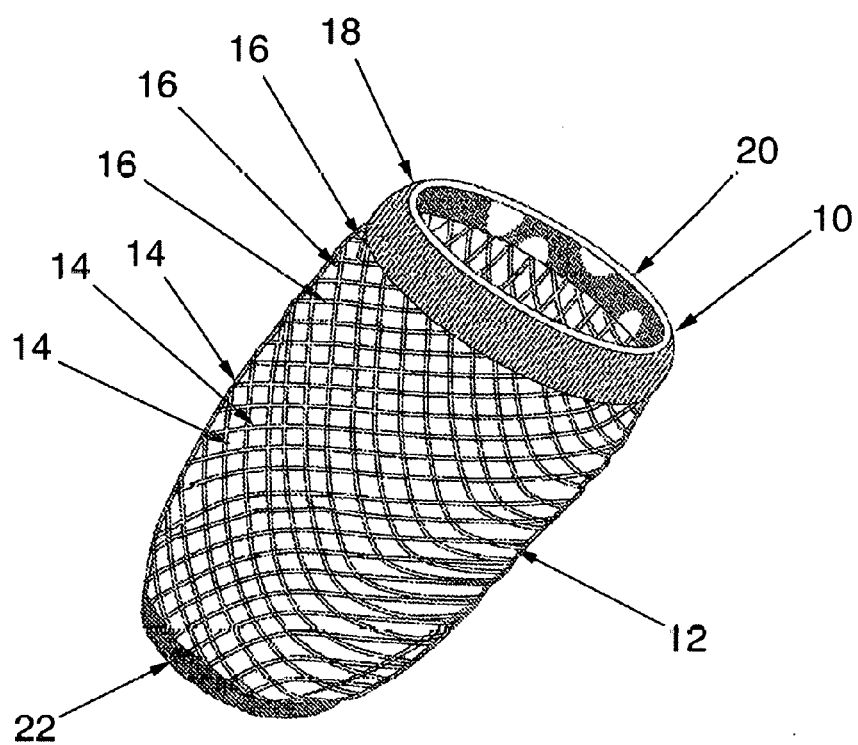
FIG. 1 is a front view of a simple prosthetic device embodying the present invention.

In that form of the present invention chosen for purposes of illustration, FIG. 1 shows a prosthetic device, indicated generally at 10, comprising a sleeve 12 formed of moderately elastic material formed with a plurality of openings 14 arranged in parallel rows 16 extending diagonally over most of the sleeve 12. The sleeve 12 has a cuff portion 18 located at an open first end 20 and the opposite end 22 is sealed.

Figure 4:
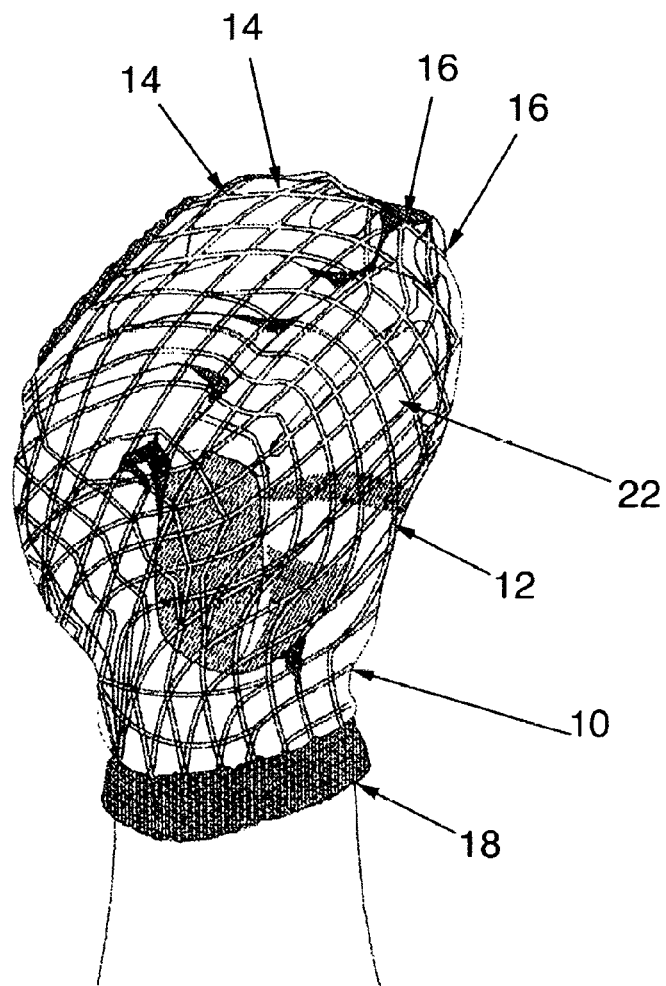
FIG. 4 is a front view of the prosthetic device of FIG. 1 showing a patient holding a bar of soap.
Figure 5:
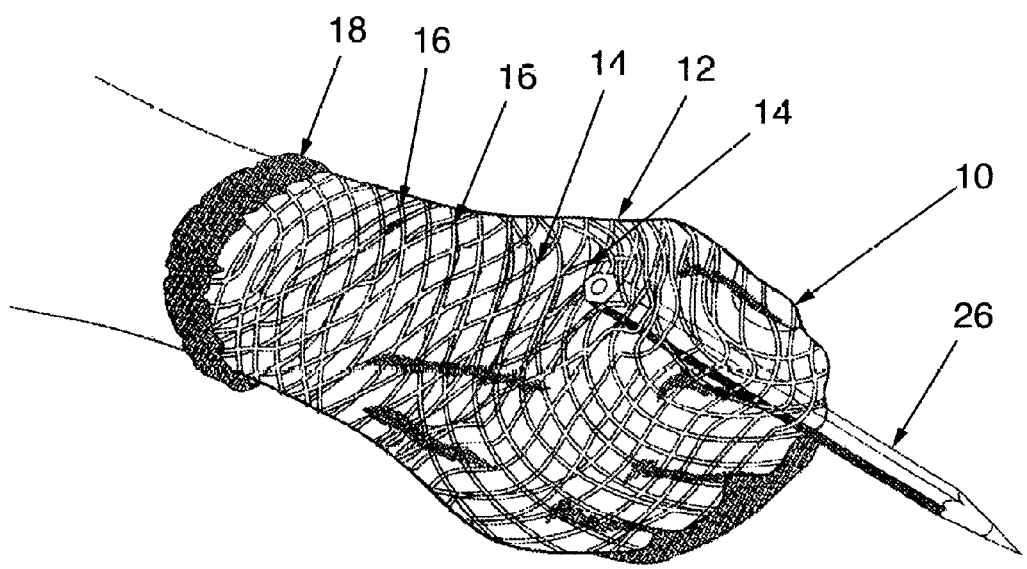
FIG. 5 is an isometric view showing a patient using the prosthetic device of FIG. 1 to hold a pen.
Figure 6:
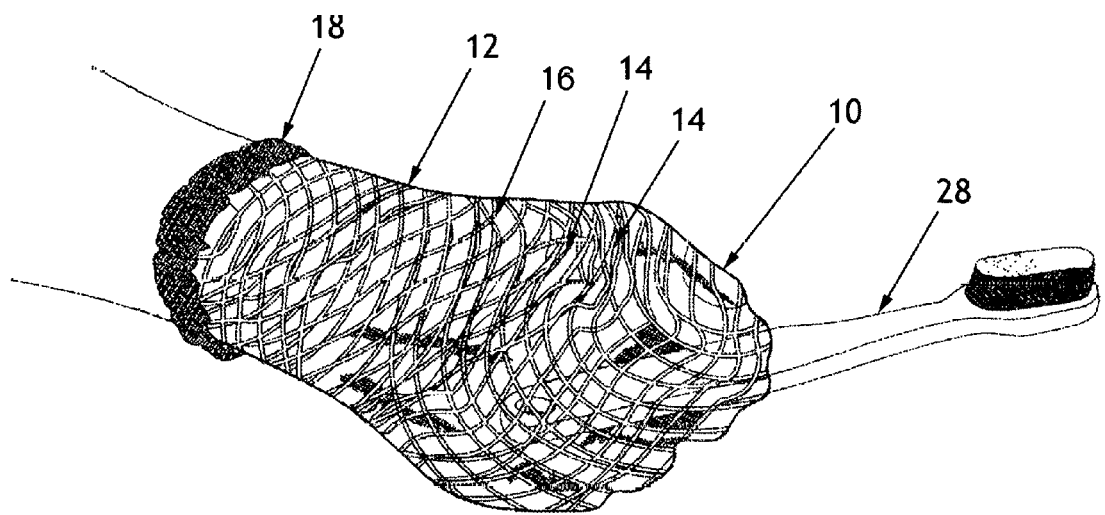
FIG. 6 is an isometric view showing a patient using the prosthetic device of FIG. 1 to hold a tooth brush.

In whether the patient has a full hand, a partial hand or a forearm stump, the patient can pull the sleeve 12 over what he has, as one would pull on a mitten or sock, to enable him to perform many activities which would otherwise be impossible for him. Thus, FIG. 4 shows the patient using the sleeve 12 to hold a bar of soap 24. Because the bar of soap 24 becomes extremely slippery when wet, manually challenged patients often have great difficulty retaining the bar of soap and, if it slips out of their grasp, it can be very difficult to retrieve in a bathtub and, in a shower, can easily be stepped on causing the patient to fall resulting in possible injury or even death. With the prosthetic device 10 holding the bar of soap 24, as shown in FIG. 1, the bar of soap 24 cannot escape from the prosthetic device 10 which eliminates these problems. Similarly, FIG. 5 sows a patient using the prosthetic device 10 to hold a tool, such as a pencil 26. The pencil 26 is woven through the openings 14 in a manner to hold the pencil 26 firmly in a position which enables the patient to manipulate the pencil 26 using only his shoulder muscles, if necessary. Also, FIG. 6 shows the patient using the prosthetic device 10 to hold a tooth brush 28. Obviously any of the foregoing tasks would be extremely difficult or impossible for a manually challenged patient to preform without assistance. However, these and many other tasks are possible for the patient using the prosthetic device 10 of the present invention. Also, the prosthetic device 10 is quite inexpensive and can be put on and taken off very easily with little or no assistance. Thus, while a patient is waiting to receive a more sophisticated prosthetic device, they can use the prosthetic device 10. Also, since the more sophisticated prosthetic devices require considerably greater time and effort to apply and remove, the prosthetic device 10 can be extremely useful even after the patient has received the more sophisticated device.

Figure 2:
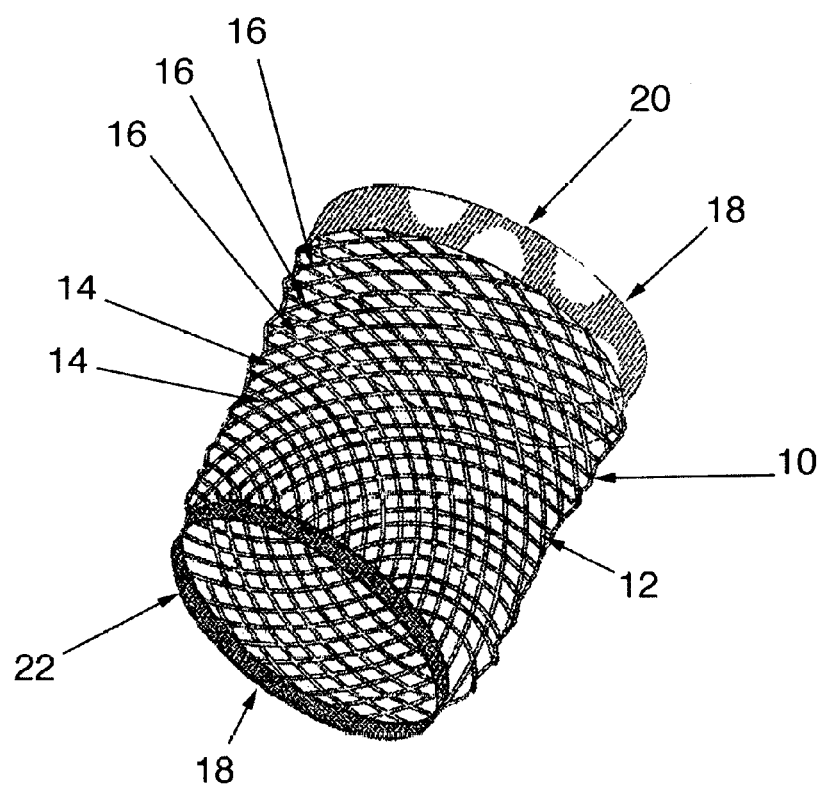
FIG. 2 is a front view of an alternative form of the prosthetic device of FIG. 1.
Figure 7:
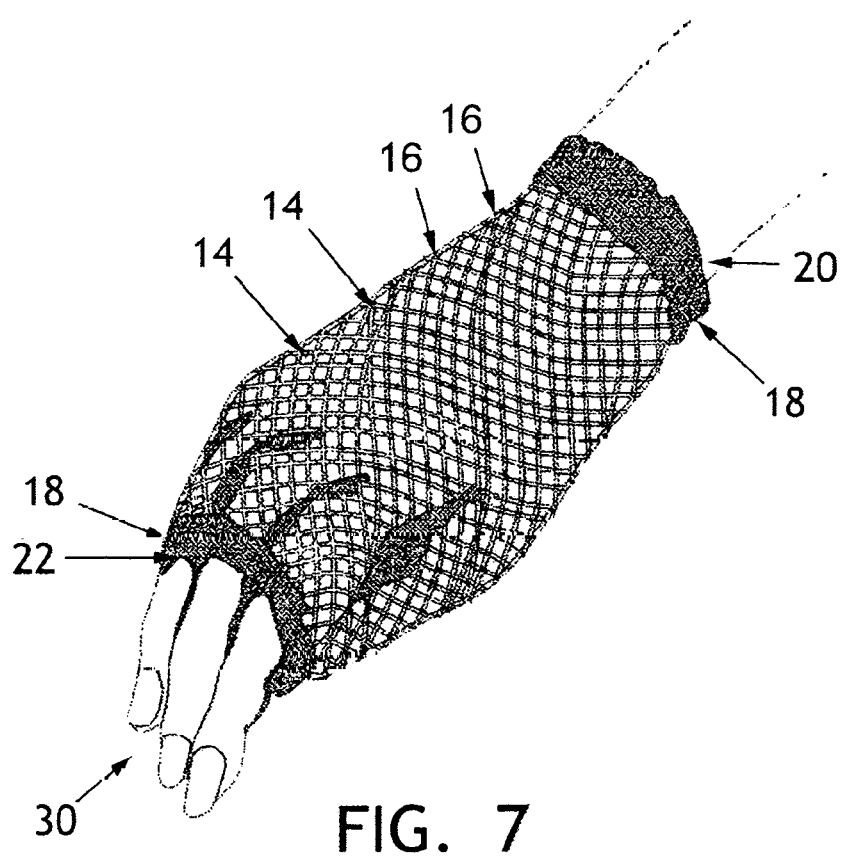
FIG. 7 is an isomeric view showing a patient using the prosthetic device of FIG. 2.

FIG. 2 shows an alternative form of the prosthetic device 10 wherein the sleeve 12 has cuffs 18 at both ends. This form of the present invention is useful for patients who still have all or some of their fingers, especially where the fingers are partially or completely paralyzed. This form of the prosthetic device 10 is used in the same manner as described above, except that some or all of the patient's fingers project through an aperture 34 formed at the open end 22, FIG. 2, of sleeve 12, as seen at 30 in FIG. 7.

Figure 3:
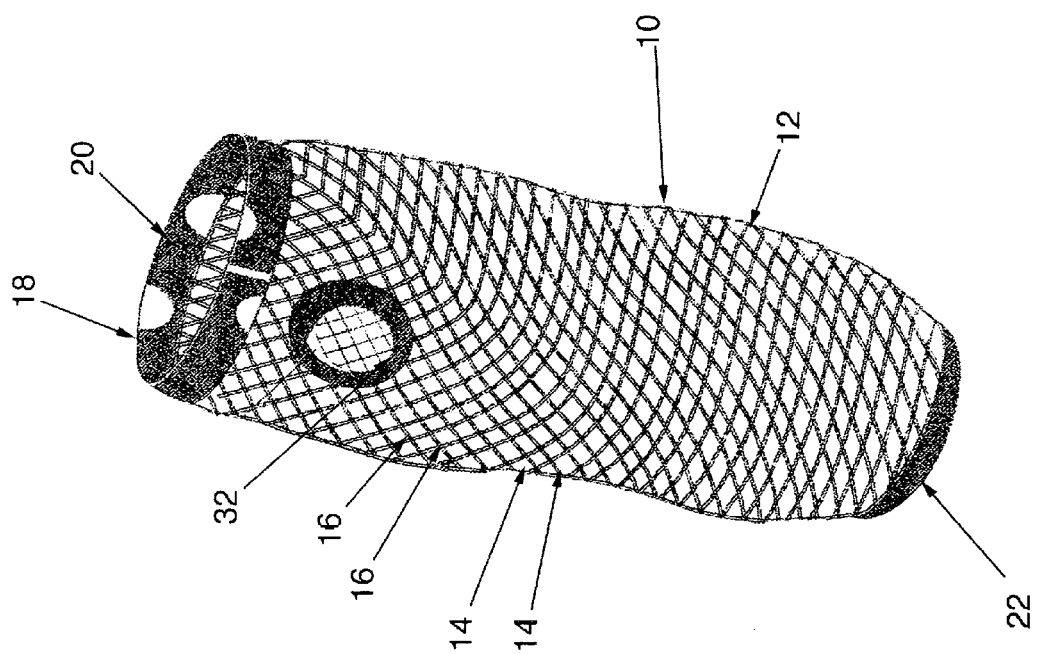
FIG. 3 is a front view of another alternative form of the prosthetic device of FIG. 1.

FIG. 3 shows another alternative form of the prosthetic device 10 wherein the sleeve 12 is elongated and an orifice 32 is formed adjacent the cuff 18, while end 22 is sealed as in the form of FIG. 1. This form of the prosthetic device 10 is useful for patients who have large hands who may find the device of FIG. 1 uncomfortably confining. In use, this form of the prosthetic device is pulled over the patient's hand and the extraneous portion is pulled back and tucked through the orifice opening 32. In use, this form of the prosthetic device 10 is the same as described above with respect to FIG. 1.

Obviously, numerous other variations and modifications can be made without departing from the spirit of the present invention. Therefore, it should be clearly understood that the forms of the parent invention described above and shown in the figures of the accompanying drawing are illustrative only and are not intended to limit the scope of the present invention.

What is claimed is:

1. A method of enabling a manually challenged patient to grip and maneuver a tool using primarily shoulder muscles, the method comprising:

provided a prosthetic device comprising a sleeve formed from elastic mesh material comprising a plurality of openings, the sleeve including a cuff located at each end of the sleeve;

stretching the sleeve over a hand or forearm stump of the patient;

weaving the tool through several of the plurality of openings on the sleeve to firmly hold the tool in a position that enables the patient to manually manipulate the tool for use; and manipulating the tool using the shoulder muscles primarily.

* * * * *